US007469161B1

(12) United States Patent
Gandhi et al.

(10) Patent No.: US 7,469,161 B1
(45) Date of Patent: Dec. 23, 2008

(54) SYSTEMS AND METHODS FOR MONITORING AND MANAGING POWER CONSUMPTION OF AN IMPLANTABLE MEDICAL DEVICE

(75) Inventors: Raj Gandhi, Woodbury, MN (US); Jonathan Kelly, Cottage Grove, MN (US); Derek Bohn, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 493 days.

(21) Appl. No.: 11/015,429

(22) Filed: Dec. 16, 2004

(51) Int. Cl.
*A61N 1/02* (2006.01)

(52) U.S. Cl. .................. 607/29; 607/1; 607/2; 607/28; 607/32; 607/60; 607/115; 128/897; 128/898; 128/899

(58) Field of Classification Search ............... 607/1–5, 607/9, 27–29, 31–32, 60, 115–116, 119; 128/897–899; 324/426; 702/63
See application file for complete search history.

(56) References Cited

U.S. PATENT DOCUMENTS

| | | | | |
|---|---|---|---|---|
| 4,556,061 A | * | 12/1985 | Barreras et al. ............... | 607/32 |
| 5,925,001 A | * | 7/1999 | Hoyt et al. .................. | 600/595 |
| 6,664,763 B2 | * | 12/2003 | Echarri et al. ............... | 320/132 |
| 6,671,552 B2 | | 12/2003 | Merritt et al. | |
| 6,804,557 B1 | | 10/2004 | Kroll | |
| 7,123,964 B2 | | 10/2006 | Betzold et al. | |
| 2002/0140399 A1 | * | 10/2002 | Echarri et al. ............... | 320/130 |
| 2003/0114897 A1 | | 6/2003 | Von Arx et al. | |
| 2003/0114898 A1 | | 6/2003 | Von Arx et al. | |
| 2003/0130708 A1 | | 7/2003 | Von Arx et al. | |
| 2003/0149459 A1 | | 8/2003 | Von Arx et al. | |
| 2004/0039424 A1 | | 2/2004 | Merritt et al. | |

OTHER PUBLICATIONS

U.S. Appl. No. 10/915,903, filed Aug. 10, 2004.
U.S. Appl. No. 11/684,820, filed Mar. 12, 2007.
Advisory Action dated Jul. 31, 2008, from Examiner George C. Manuel, Art Unit 3762, for U.S. Appl. No. 10/915,903 (3 pgs.).*
Amendment after Final Rejection dated Jun. 17, 2008 from Attorney Victor P. Jonas, for U.S. Appl. No. 10/915,903 (13 pgs.).*

* cited by examiner

*Primary Examiner*—Carl H. Layno
*Assistant Examiner*—Deborah Malamud
(74) *Attorney, Agent, or Firm*—Faegre & Benson LLP

(57) ABSTRACT

In one embodiment, an external programming device is operable to determine and graphically display power consumption of an implantable medical device ("IMD"). In accordance with this particular embodiment, the external programming device includes a graphical user interface display and a communication interface operable to receive information from an IMD. In this embodiment, the external programming device is operable to receive IMD parameter settings and/or battery parameter values from the IMD, calculate an power consumption rate for the IMD, and then display the power consumption on the graphical user interface display using a graphical visual indicator.

22 Claims, 7 Drawing Sheets

SYSTEMS AND METHODS FOR MONITORING AND MANAGING POWER CONSUMPTION OF AN IMPLANTABLE MEDICAL DEVICE

BACKGROUND OF THE INVENTION

The present invention relates generally to systems and methods for monitoring, configuring and managing implantable medical devices ("IMDs"), and more particularly, to systems and methods for monitoring and managing power consumption of the IMDs.

Cardiac pacemakers, implantable cardioverter defibrillators ("ICDs"), and cardiac resynchronization therapy ("CRT") devices are all implantable medical devices ("IMDs"). Pacemakers are designed to emit pacing stimuli to one or more chambers of the heart to treat bradyarrythmia. ICDs typically have pacemaker functions and also include high voltage output capability that can be used to treat potentially lethal tachyarrhythmias. CRT devices provide pacing therapy to synchronize the left and right ventricles as a treatment for heart failure. CRT devices may or may not have high voltage defibrillation capability (CRT-P or CRT-D).

These IMDs are battery powered and, once implanted, require regular follow-up by a physician or health care professional to assess proper system operation and continued remaining battery capacity. The follow-ups typically occur at regular intervals, for example, every six months. Modern IMDs can communicate with an external computing device in a bi-directional fashion. This external computing device, known as a "programmer" or a programmer/recorder/monitor ("PRM") allows the physician or health care professional to retrieve various diagnostic data, review stored history about the patient and device operation, and change various parameters of the device. The PRM also can show information related to battery status.

Batteries for IMDs typically use lithium iodide (LiI), lithium silver vanadium pentoxide (LiSVO), or lithium carbon monoflouride (LiCFx) chemistries. Depending on the chemistry, battery depletion status can be assessed by the device by measuring battery voltage, the time required to charge internal capacitors, use of a coulomb charge counter, or some a combination of these or other methods. Specific algorithms for determining battery status vary by manufacturer, chemistry, and individual device.

Overall longevity for IMDs typically is estimated during the product development cycle. Models of battery capacity, expected variations in circuit performance, and clinical use conditions are all taken into account in these models. From this modeling effort, longevity estimates are created for various assumed clinical use conditions. The Instructions for Use (IFU) that are included in the finished device packaging and labeling will contain these battery longevity estimates.

During the life of the device, the estimated battery longevity remaining may be determined from a simple calculation of the estimated total longevity minus the portion of life already consumed from the battery. Many IMDs currently marketed can make such calculations and display them to the user through a programmer.

The longevity of an IMD may vary widely depending upon clinical use conditions. The programmed amplitude of pacing pulses, for example, can affect CRT device longevity by a factor of two or more (i.e., half the typical lifetime), depending on the number of pacing pulses the CRT device emits. Many physicians and health care professionals are surprised at the impact these clinical use conditions and parameter settings have on device longevity and express displeasure when overall longevity varies significantly from typical values.

Thus, a need exists for a systems, methods, and/or devices that can inform physicians or health care professionals of the IMD's power consumption, which in some instances, can effect the IMD's battery longevity, and can allow the physicians or health care providers to understand (and perhaps modify) specific parameters that are causing the power consumption levels.

BRIEF SUMMARY OF THE INVENTION

In one embodiment, the present invention relates to an external programming device operable to determine and graphically display power consumption of an implantable medical device ("IMD"). In accordance with this particular embodiment, the external programming device includes a graphical user interface display and a communication interface operable to receive information from an IMD. In this embodiment, the external programming device is operable to receive IMD parameter settings and/or battery parameter values from the IMD, calculate an power consumption rate for the IMD, and then display the power consumption on the graphical user interface display using a graphical visual indicator.

In one embodiment of the invention, the IMD can be a cardiac rhythm management device, such as a pacemaker, an implantable cardioverter defibrillator ("ICD"), a pacer/defibrillator, or a cardiac resynchronization ("CRT") device. Further, in some embodiments, the external programming device can calculate the power consumption for the IMD using IMD parameters, such as lead impedance, pace or sense rate, programmed pulse width, programmed pulse amplitude, and/or load parameters of are or more sensors associated with the IMD.

In still other embodiments, the external programming device can be operable to determine whether the power consumption is sub-optimal. If it is, the external programming device then is operable to identify one or more parameters that might be contributing to the sub-optimal power consumption. The external programming device then can receive commands to adjust at least one of the parameters that might be contributing to the sub-optimal power consumption. Upon receiving the command, the external programming device then can adjust the parameter, calculate an adjusted power consumption for the IMD using the adjusted parameter, and display the adjusted power consumption on the graphical visual indicator In accordance with the present invention, the graphical visual indicator can be any graphical visual indicator currently existing or hereinafter developed. In accordance with some embodiments, however, the graphical visual indicator can be, for example, a level indicator, a multi-colored display, a gray-scale display, a multi-size indicator, a radial indicator or a pie indicator, to name a few. In one embodiment, the graphical visual indicator can be a three-color display, where the first color on the display indicates an power consumption rate, the second color on the display indicates an elevated power consumption rate, and the third color on the display indicates a high power consumption rate. In yet another embodiment, the graphical visual indicator can be a multi-level display where the first level on the display indicates an power consumption rate, the second level on the display indicates an elevated power consumption rate, and the third level on the display indicates a high power consumption rate. In accordance with this embodiment, each level on the display can include one or more level indicators within each level. In addition, each level indicator can be indicative of a power consumption rate.

In accordance with another embodiment, the present invention relates to a method for assessing and graphically displaying power consumption rate for an implantable medical device ("IMD") battery. In accordance with this embodiment, an IMD is operable to communicate IMD parameter setting and/or battery values to an external programming device. The external programming device then is operable to calculate an power consumption rate for the IMD, and display the power consumption rate on a graphical user interface display using a graphical visual indicator. In accordance with another embodiment, the present invention relates to yet another method for assessing and graphically displaying power consumption rate for an implantable medical device ("IMD") battery. In accordance with this embodiment, an IMD is operable to calculate a power consumption rate using IMD parameter setting and/or battery values. The IMD then is operable to communicate the power consumption rate to an external programming device, which in turn, can display the power consumption rate on a graphical user interface display using a graphical visual indicator.

In still another embodiment, regardless of whether the IMD or the external programming device calculates the power consumption value, the external programming device further can be operable to determine whether the power consumption rate is sub-optimal. If it is, the external programming device then can identify one or more parameters that might be contributing to the sub-optimal power consumption. The external programming device then can receive commands to change one or more of the parameters that might be contributing to the sub-optimal power consumption. After parameters have been changed, the IMD and/or the external programming device can calculate an adjusted power consumption for the IMD using the one or more adjusted parameters. The external programming device can then display the adjusted power consumption on the graphical visual indicator.

A more complete understanding of the present invention may be derived by referring to the detailed description of preferred embodiments and claims when considered in connection with the figures.

BRIEF DESCRIPTION OF THE DRAWINGS

In the Figures, similar components and/or features may have the same reference label. Further, various components of the same type may be distinguished by following the reference label with a second label that distinguishes among the similar components. If only the first reference label is used in the specification, the description is applicable to any one of the similar components having the same first reference label irrespective of the second reference label.

DETAILED DESCRIPTION OF THE INVENTION

The present invention relates generally to systems and methods for monitoring, configuring and managing implantable medical devices, and more particularly, to systems and methods for monitoring and managing power consumption of the implantable medical devices.

In one embodiment, the purpose of this invention not only is to inform physicians or health care professionals of the IMD power consumption rate, it also is to specifically draw their attention to situations in which power consumption rate is greater than for typical or devices. Further, in some embodiments, the present invention can enable the physicians or health care professionals to understand, monitor and/or modify specific parameters that are causing the greater than expected power consumption rate.

The description herein discusses the invention with reference to power. As one skilled in the art would appreciate, however, power is a function of voltage and current therefore, the present invention can measure, calculate and/or display these parameters as well. Thus, the present invention is not limited to straight power measurements and calculations per se.

In some embodiments, the system (and/or methods) of the present invention can work in conjunction with existing algorithms for calculating and/or displaying IMD power consumption rates and remaining device battery longevity estimates. For example, one embodiment of a method for estimating or determining remaining battery longevity for IMDs is disclosed in U.S. patent application Ser. No. 10/915,903, filed on Aug. 10, 2004, and entitled "Systems and Methods for Managing the Longevity of an Implantable Medical Device Battery," the entirety of which is incorporated by reference herein for all purposes. Further, as one skilled in the art will appreciate, other power consumption rate and longevity calculations can be used. Thus, in accordance with known or hereinafter developed power consumption and longevity calculation techniques, embodiments of systems and methods of the present invention can calculate the power consumption rate and display this rate to a user, for example, via a graphical visual indicator. The system then allows the user to navigate to another screen in the programmer, which can display the current values of the various parameters that might be influencing the power consumption rate. The user then is allowed to enter changes to those parameters to determine what impact the changes would have to the power consumption rate (which again can be displayed on the graphical visual indicator). The user then is allowed to make additional changes to the parameters, if appropriate. The result is that during patient visits, the physician or health care professional can easily observe conditions that may lead to a high power consumption rates, and can be given an opportunity to make changes to IMD parameters that might improve the power consumption rate, and thus, the longevity of the IMD battery.

Figure 1:
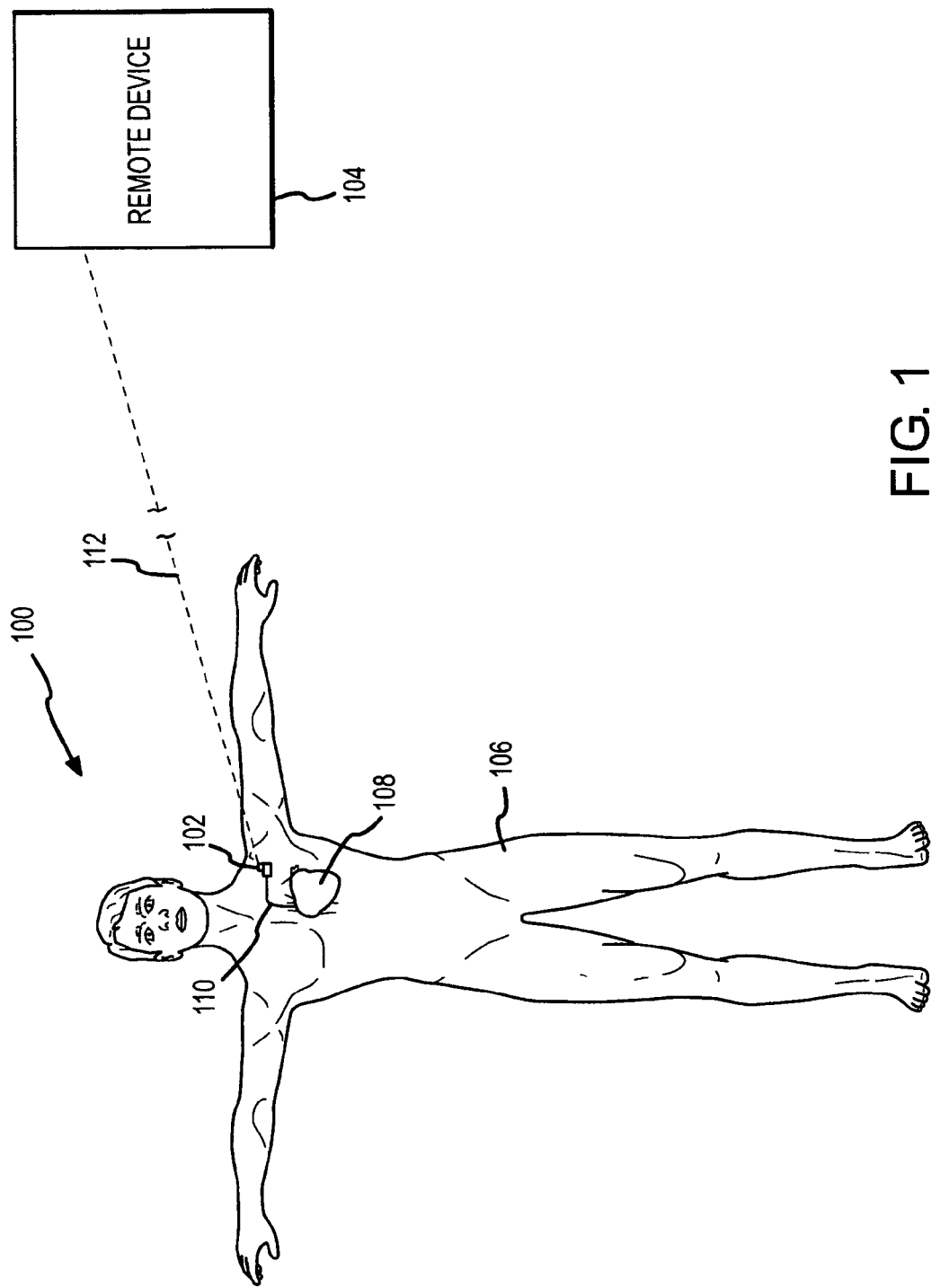
FIG. 1 is a schematic drawing showing one embodiment of a system, including an implantable medical device ("IMD"), that can be used to monitor and manage battery longevity for an IMD battery.

Referring now to FIG. 1, one embodiment of a system 100 for monitoring and managing battery longevity of an implantable medical device is shown. In accordance with the illustrated embodiment, system 100 includes an implantable medical device ("IMD") 102 and an external programming device 104. IMD 102 and external programming device 104 can communicate via a wireless communication link 112.

IMD 102 can be any type of implantable medical device that includes a battery. For example, IMD 102 can be cardiac rhythm management device ("CRM"), a ventricular assist blood pump, a drug delivery pump, a drug infusion device, a neurostimulating device, or any other suitable implantable device that includes a battery. In the embodiment illustrated in FIG. 1, IMD 102 is a CRM device, which is implanted within a patient's body 106 and coupled to the patient's heart 108 by a lead system 110. Examples of implanted CRM devices 102 include (but are not limited to) pacemakers, cardiac resynchronization ("CRT") devices, implantable cardioverter/defibrillators ("ICDs"), pacer/defibrillators, and the like.

Figure 2:
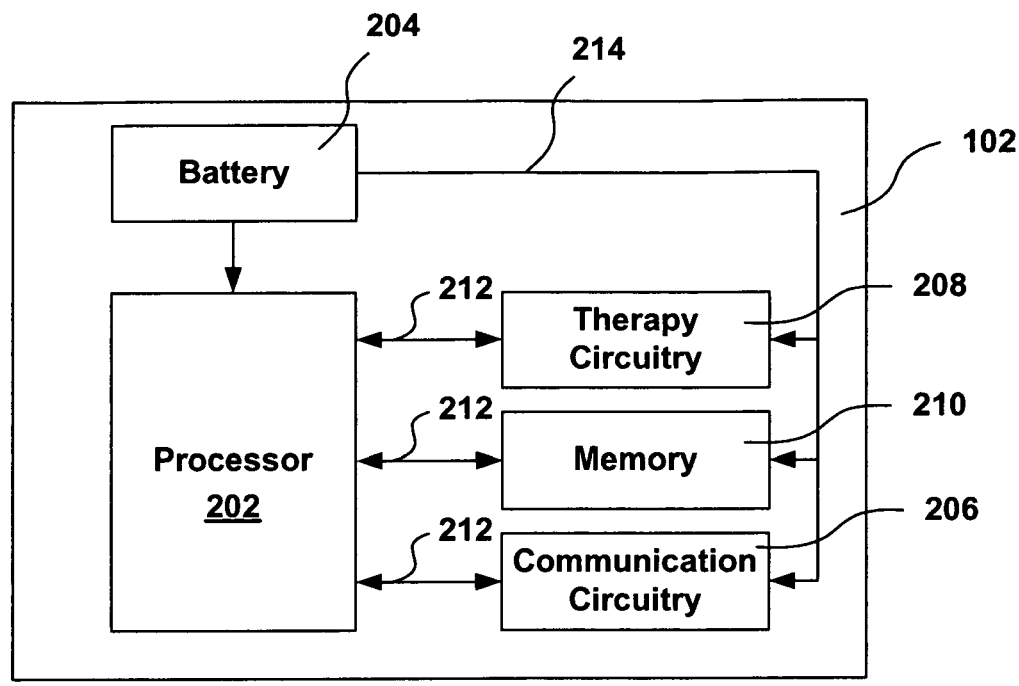
FIG. 2 is a block diagram showing some components of one embodiment of an IMD that can be used in the present invention.

Referring now to FIG. 2, one embodiment of an IMD 102 is illustrated. In accordance with the illustrated embodiment, IMD 102 comprises a processor 202, a battery 204, communication circuitry 206, therapy circuitry 208, and a memory 210. Communication circuitry 206, therapy circuitry 208 and memory 210 all are in electrical communication with processor 202, as is illustrated by arrows 212. In addition, battery 204 is configured to provide power to some or all the power consuming components within IMD 102. In the illustrated embodiment, for example, battery 204 provides power to communication circuitry 206, therapy circuitry 208 and memory 210 via electrical connection 214. In addition, as illustrated, processor 202 can receive power, as well as other battery parameters, such as current drain, depth of discharge, etc., from battery 204 via connection 216. As discussed in more detail below, the battery parameters can be used to determine battery longevity and other battery statistics.

As one skilled in the art will appreciate, processors and memory devices are well known in the art, and the specific type and/or style of processor or memory device that can be used in IMD 102 is not limited. Accordingly, processor 202 can be any suitable processing device currently known or hereinafter developed, and memory device 210 can be any suitable memory device currently known or hereinafter developed.

Communication circuitry 206 is circuitry that allows IMD 102 to communicate with other devices, such as external programming device 104, other IMDs, or other external devices. As discussed above, IMD 102 communicates with other devices via a wireless connection; e.g., wireless communication link 112. The wireless connection can be, for example, a near-field radio frequency (RF) communication connection, a far-field RF communication connection, an acoustical communication connection, an optical communication connection, or any other suitable wireless communication connection.

In one embodiment, communication circuitry 206 can include circuitry for both near-field RF telemetry and far-field RF telemetry. For example, one embodiment of communication circuitry that can be used in IMD 102 is disclosed in Published U.S. Patent App. No. US 2003/0114897 A1, published on Jun. 19, 2003, and entitled "Implantable Medical Device with Two or More Telemetry Systems," and Published U.S. Patent App. No. U.S. 2003/0114898 A1, published on Jun. 19, 2003, and entitled "Telemetry Duty Cycle Management System for an Implantable Medical Device," both of which are incorporated by reference herein for all purposes.

In addition, in other embodiments, power saving wireless communication circuitry and methods can be used. For example, the IMD communication circuitry 206 can be configured to reside in a power-saving, sleep mode for a majority of the time. In accordance with this embodiment, communication circuitry 206 can be configured to "wake-up" on a periodic basis to communicate with an external device. Upon "wake-up" the external device will monitor for RF activity, and if the external device locates it, communication between the IMD and the external device can be initiated. There are a number of different ways IMD power-saving modes can be implemented, and the present invention is not limited to any particular one. Indeed, the aforementioned Published U.S. Patent App. Nos. US 2003/0114897 A1 and US 2003/0114898 A1 disclose different ways of implementing IMD power-saving modes, which, as discussed above, are incorporated herein by reference for all purposes. In addition, alternative embodiments of power management systems and methods that can be used in the present invention are disclosed in Published U.S. Patent App. No. US 2003/0149459 A1, published on Aug. 7, 2003, and entitled "Methods and Apparatuses for Implantable Medical Device Telemetry Power Management," the entirety of which is incorporated by reference herein for all purposes.

Further, in accordance with other embodiments, communication circuitry 206 can be configured to communicate with an intermediary telemetry device, which, in turn, can facilitate communication with external programming device 104. One example of this type of configuration is disclosed in Published U.S. Patent App. No. US 2003/0130708, published on Jul. 10, 2003, and entitled "Two-Hop Telemetry Interface for Medical Device," the entirety of which is incorporated by reference herein for all purposes. Further, other configurations for RF telemetry are known, and communication circuitry 206 can embody those configurations, as well. Thus, as one skilled in the art will appreciate, communication circuitry 206 is not limited by any particular configuration or communication means.

Therapy circuitry 208 comprises circuitry for providing one or more therapeutic functions to a patient. For example, therapy circuitry 208 can include circuitry for providing heart pacing therapy, cardiac defibrillation therapy, and/or cardiac resynchronization therapy, drug delivery therapy, or any other therapy associated with a suitable IMD. In the case of cardiac therapy (e.g., pacing, defibrillation, etc.), therapy circuitry 208 includes cardiac leads 110 for delivering the therapy to particular locations in the heart.

In the embodiment illustrated in FIG. 1, external programming device 104 provides a user interface for system 100. The user interface allows a physician or other healthcare provider or caregiver to interact with IMD 102 through a wireless communication link 112. Wireless communication link 112 provides for bi-directional data communication between implanted CRM device 102 and external programming device 104, and as discussed above, can comprise any suitable wireless communication link 112, such as, a near-field RF communication connection, a far-field RF communication connection, an acoustical communication connection, an optical communication connection, or any other suitable wireless communication connection.

In one embodiment, RF telemetry link 112 provides for data transmission from IMD 102 to external programming device 104. This may include, for example, transmitting real-time physiological data acquired by IMD 102, extracting physiological data acquired by and stored in IMD 102, extracting therapy history data stored in IMD 102, and extracting data indicating an operational status of IDM 102 (e.g., lead impedance, battery status, battery longevity information, etc.). In addition, wireless communication link 112 can transmit data from external programming device 104 to IMD 102. This may include, for example, programming IMD 102 to acquire physiological data, programming IMD 102 to perform at least one self-diagnostic test (such as for a device operational status), programming IMD 102 to deliver at least one therapy, or changing one or more therapy parameter for the IMD.

Figure 3:
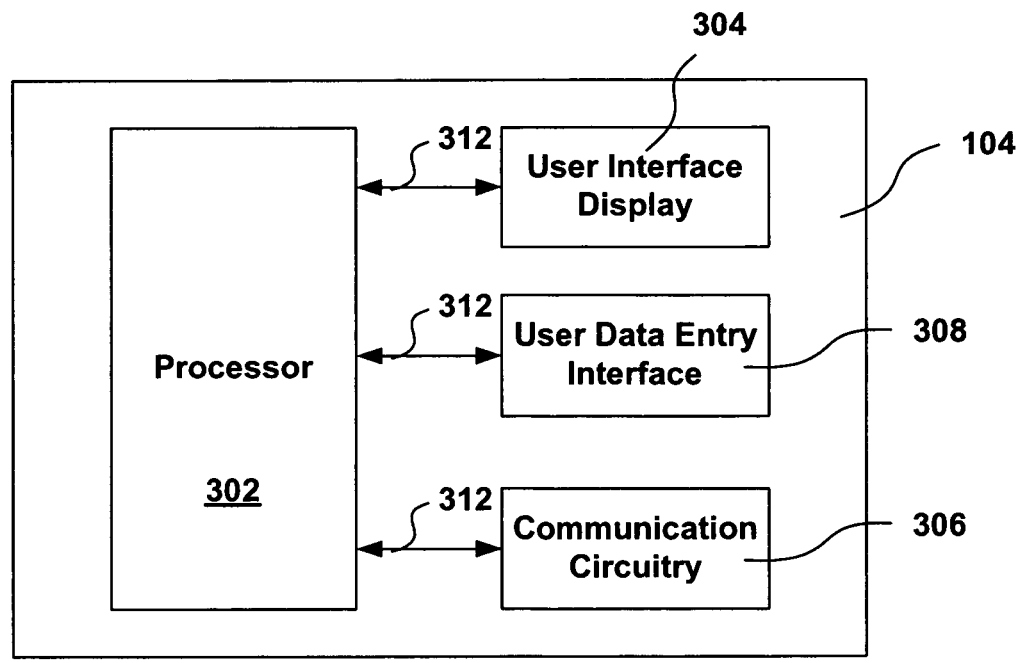
FIG. 3 is a block diagram showing some components of one embodiment of an external programming device that can be used with the present invention.

Referring now to FIG. 3, one embodiment of an external programming device 104 is shown. In the illustrated embodiment, external programming device 104 comprises a processor 302 (and associated memory (not shown)), a user interface display 304, communication circuitry 306 and a user date entry interface 308. User interface display 304, communication circuitry 306, and patient interface 308 all are in electrical communication with processor 302, as is illustrated by arrows 312.

As one skilled in the art will appreciate, and as discussed above with reference to IMD 102, processors and memory devices are well known in the art, and the specific type and/or style of processor or memory devices that can be used in external programming device 104 are not limited. Accordingly, processor 302 can be any suitable processing device currently known or hereinafter developed. Similarly, the memory (not shown) can be any suitable memory device currently known or hereinafter developed.

In addition, communication circuitry 306 is circuitry that allows external programming device 104 to communicate with IMD 102, and perhaps other devices. Thus, if IMD 102 is communicating via an RF connection, communication circuitry 306 comprises RF communication circuitry, as well. Similarly, if optical or acoustical communication connections are used, communication circuitry 306 is adapted to facilitate such connections. Thus, communication circuitry 306 can be any circuitry adapted to facilitate the wireless communications with IMD 102. As one skilled in the art will appreciate, such circuitry is known in the art, and therefore, will not be discussed in detail herein.

In the embodiment illustrated in FIG. 3, external programming device 104 includes a user interface display 304 and a user data entry interface 308, both of which facilitate communication with a user, such as a physician, or other health care provider or caregiver. For example, user interface display 304 is adapted to visually display or otherwise communicate various different IMD parameters and information for a user to view, and can be an electronic graphical user interface, a print-out display, or any other suitable interface display. Such interfaces are well known in the art, and thus, the present invention is not limited to any particular interface display. Examples of a few visual screens that may be displayed by user interface display 304 are shown in FIGS. 7-9, and are discussed in more detail below.

Similarly, user data entry interface 308 is an interface that allows a user to enter data and/or adjust IMD parameter values. Data entry interface 308 can be a keyboard device, a mouse, a touch screen, voice recognition technology, or any other suitable data entry interface. Again, data entry interfaces are well known in the art, and thus, the present invention is not limited to any particular data entry device or technology.

Figure 4:
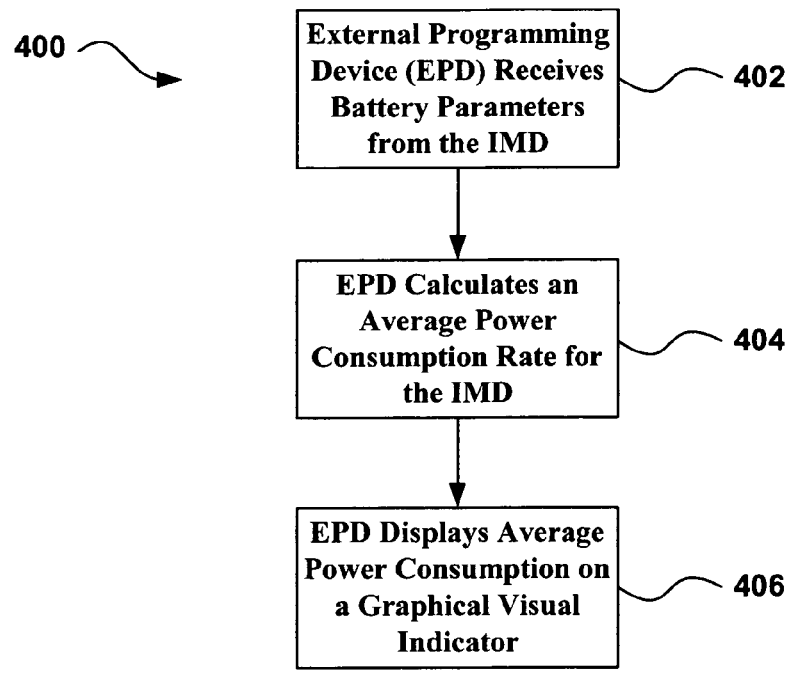
FIG. 4 is a flow-chart illustrating one embodiment of a method for determining and displaying power consumption of an IMD battery.

Referring now to FIG. 4, one embodiment of a method for monitoring and managing power consumption rate of an implantable medical device is illustrated inflow chart 400. In accordance with the illustrated embodiment, an IMD (e.g., IMD 102 in FIG. 1) transmits one or more battery and/or power consumption parameters to an external programming device (e.g., external programming device 104 in FIG. 1) (block 402). The external programming device then calculates an power consumption rate for the IMD using the battery and/or power consumption parameters (block 404. The external programming device then can display the power consumption rate using a graphical visual indicator (block 406).

In accordance with various embodiments of the present invention, the graphical visual indicator can be any suitable display that can graphically illustrate power consumption and/or battery longevity parameters. For example, the graphical visual indicator or display can include a level indicator, a multi-colored display, a gray-scale display, a multi-size indicator, a radial indicator, a pie indicator or the like.

Figure 7A:
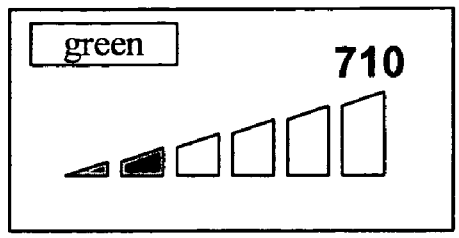
FIGS. 7a, 7b, and 7c are screen shots of embodiments of a graphical visual indicators that can be used to display power consumption of an IMD.
Figure 7B:
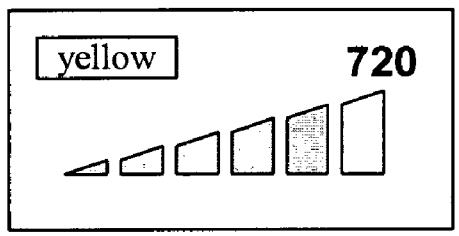
Figure 7C:
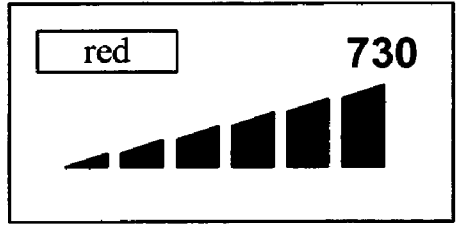

Referring now to FIGS. 7a-7c, one exemplary embodiment of a graphical visual display 700 is illustrated. In accordance with the illustrated embodiment, the power consumption of an IMD can be displayed as a multi-colored bar graph. In this particular embodiment, the multi-colored bar graph includes a plurality of bars that progressively increase in size. In addition, as more bars are illuminated, the colors can change, thus illustrating, for example, low, medium, and/or high power consumption rates. In accordance with this aspect of the invention, bar graph 710 in FIG. 7a shows two bars illuminated in green, indicating that the power consumption is low and/or normal, perhaps indicating that the battery longevity will be as expected. Further, in this exemplary embodiment, bar graph 720 in FIG. 7b shows four bars illuminated in yellow, indicating that the power consumption is elevated and/or above normal, and perhaps indicating that battery longevity might be shorter than anticipated by a physician. Finally, bar graph 730 in FIG. 7c shows all six bars illuminated in red, indicating that the power consumption is high, and thus, battery longevity might be poor. The particular example discussed herein shows two, four and six bars illuminated, respectively. One skilled in the art will appreciate, however, that three or five bars also might be illuminated, or in other embodiments, different numbers of bars and/or different colors can be used. Thus, the present invention is not limited to the embodiment illustrated in FIGS. 7a, 7b, and 7c.

Figure 8A:
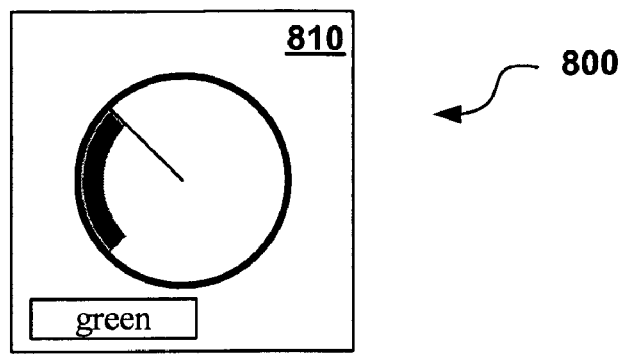
FIGS. 8a, 8b, and 8c are screen shots of other embodiments of graphical visual indicators that can be used to display power consumption of an IMD.
Figure 8B:
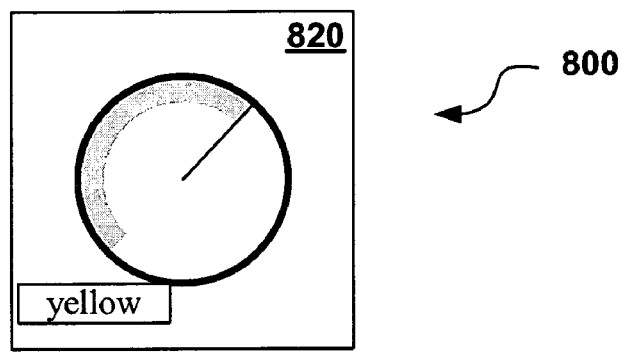
Figure 8C:
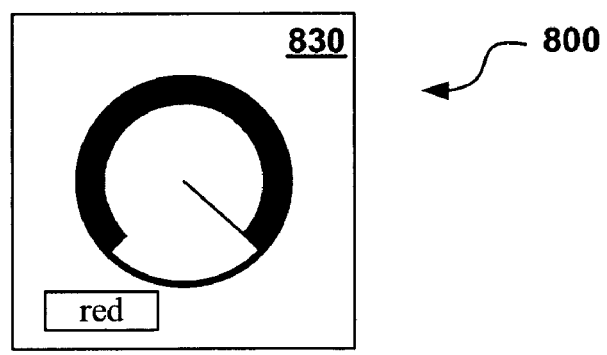
Figure 9:
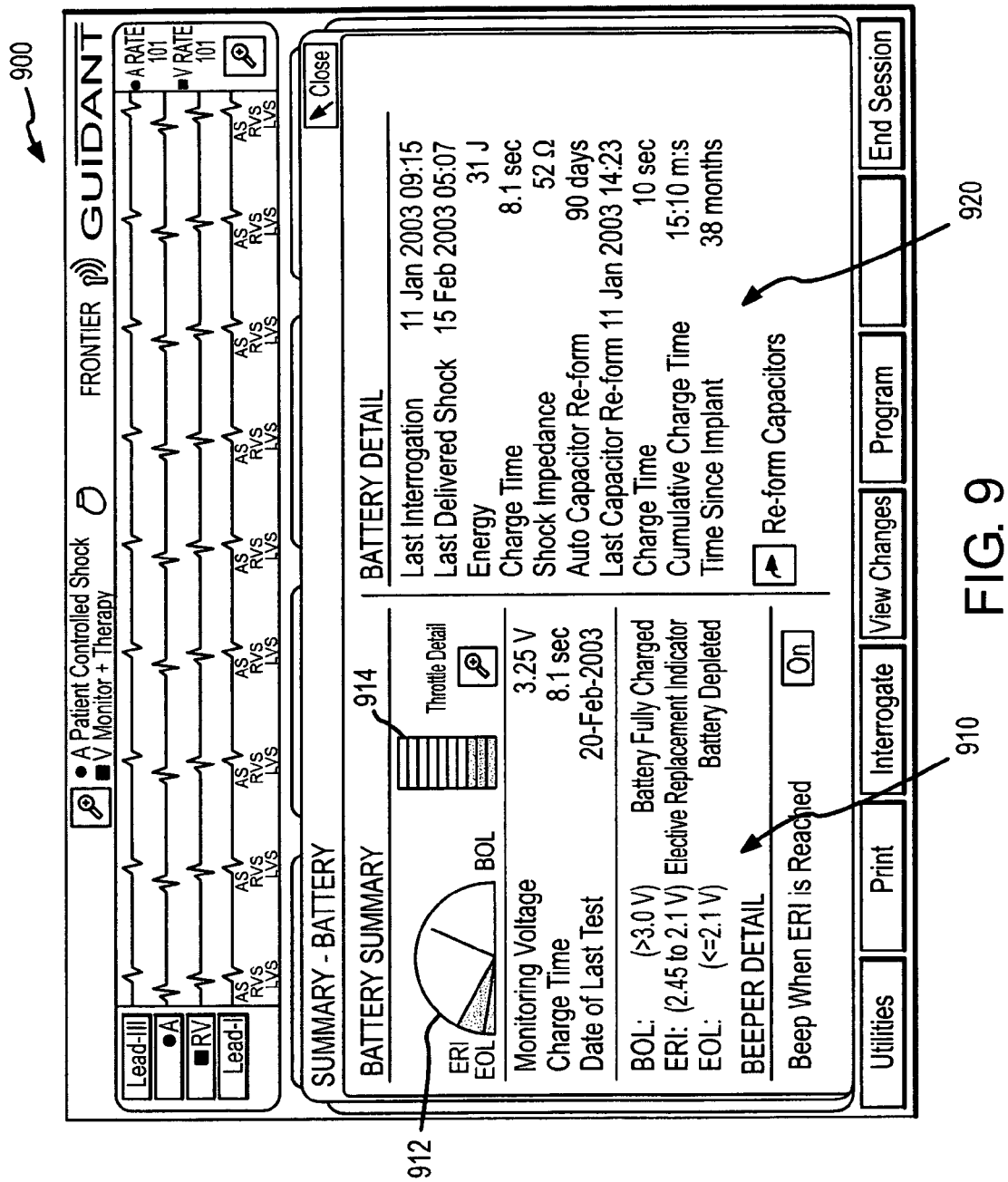
FIG. 9 is a screen shot of one embodiment of a user interface display screen that can display battery status information, including a graphical visual indicator for displaying power consumption and/or other visual interfaces for displaying IMD parameters that may be affecting the power consumption.

Referring now to FIG. 8, another embodiment of a graphical visual display 800 is illustrated. In accordance with the illustrated embodiment, the power consumption of an IMD is displayed on a graphical visual display as a semi-circular dial with a needle or line moving in a particular direction, for example from left to right. As power consumption increases, the needle or line will move and the color can change to indicate, for example, low, medium, and/or high power consumption rates. In accordance with this aspect of the invention, circular or dial graph 810 in FIG. 8a shows a semi-circular line and needle combination illuminated in green, indicating that the power consumption is low and/or normal, perhaps indicating that the battery longevity will be as expected. In this example, the semi-circle color display may be green. In FIG. 8a, the distance from the starting point reflects a short distance that the needle has moved. Further, in this exemplary embodiment, circular or dial graph 820 in FIG. 8b shows a semi-circular line and needle combination illuminated in yellow, indicating that the power consumption is elevated and/or above normal, and perhaps indicating that battery longevity might be shorter than anticipated by a physician. In FIG. 8b, the distance from the starting point reflects a medium distance that the needle has moved. Finally, circular or dial graph 830 in FIG. 8*c* shows a semi-circular in and needle combination illuminated in red, indicating that the power consumption is high, and thus, battery longevity might be poor. In FIG. 8*c*, the distance from the starting point reflects a long distance that the needle has moved. Also, as one skilled in the art will appreciate the dial graph 830 is not limited to a needle, it may be anything that reflects a change in the power consumption, such as tick marks or the like. Further, the change may be reflected in a dial where the indicator, such as a needle, moves either to the right or to the left. In addition, one skilled in the art will appreciate that other colors and other graph depictions can be used, and thus, the present invention is not limited to the embodiment illustrated in FIGS. 8*a*, 8*b*, and 8*c*.

As discussed in more detail below, after visually identifying the power consumption rate with the graphical visual indicator, a healthcare provider may be able to adjust at least one parameter contributing to the high power consumption, and then visualize the adjusted power consumption rate, for example, on multi-colored graphs 700 and 800. As discussed below, these adjustments can be made as many times as required by the healthcare provider to optimize the power consumption rate of the IMD. Further, in some embodiments, the graphical visual indicator can be used to visualize the power consumption and this rate may be used to estimate a battery longevity value (e.g., the number of years or even months an IMD will last). In one embodiment, the longevity estimates can be calculated in accordance with the systems and methods disclosed in U.S. patent application Ser. No. 10/915,903, filed on Aug. 10, 2004, and entitled "Systems and Methods for Managing the Longevity of an Implantable Medical Device Battery," the entirety of which is incorporated by reference herein for all purposes.

Figure 5:
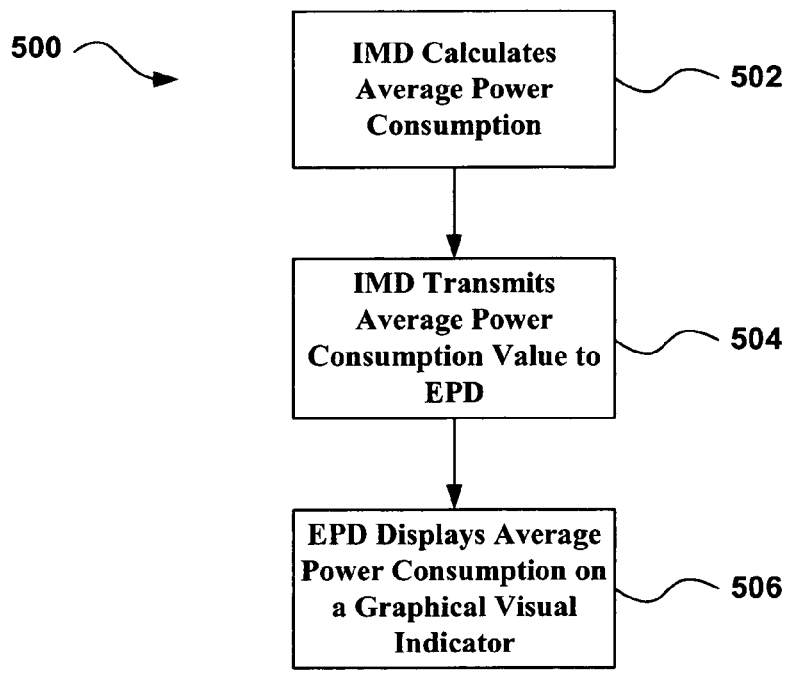
FIG. 5 is a flow-chart illustrating another embodiment of a method for determining and displaying power consumption of an IMD battery.

Referring now to FIG. 5, another embodiment of a method for monitoring and managing power consumption of an implantable medical device ("IMD") is illustrated in flow chart 500. In accordance with this particular embodiment, an IMD (e.g., IMD 102 in FIG. 1) calculates an power consumption rate using one or more parameters from the IMD and/or the IMD battery (block 510). After the IMD calculates a power consumption rate, it transmits the power consumption to an external programming device (e.g., external programming device 104 in FIG. 1) (block 520). After the external programming device receives the power consumption information, it can display the power consumption rate on a graphical visual indicator, as discussed above (block 530). Again, as discussed above, the graphical visual indicator can be any graphical visual indicator, and thus, the present invention is not limited to any particular embodiment disclosed herein.

Figure 6:
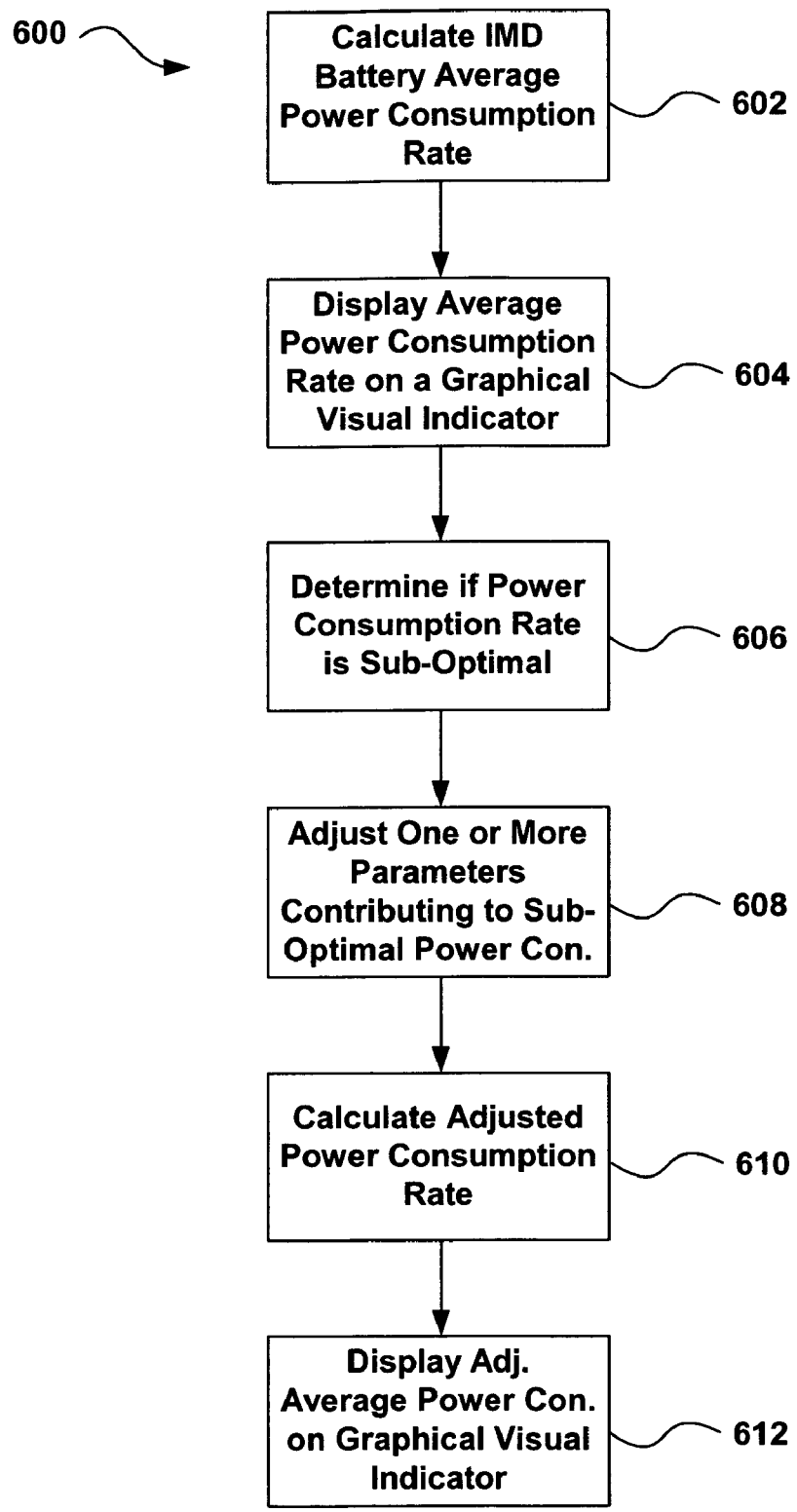
FIG. 6 is a flow-chart illustrating still another embodiment of a method for determining and displaying power consumption of an IMD battery.

Referring now to FIG. 6, another embodiment of a method for monitoring and managing power consumption of an implantable medical device ("IMD") is shown in flow chart 600. In accordance with this particular embodiment, an IMD battery power consumption rate is calculated (block 602). As discussed above with reference to FIG. 4, in one embodiment, an IMD can transmit one or more battery and/or power consumption parameters to an external programming device, which in-turn, can measure and/or calculate the power consumption rate. In an alternative embodiment discussed above with reference to FIG. 5, the IMD can measure and/or calculate the power consumption rate, and then transmit that value to the external programming device.

Regardless of which device actually calculates (and/or measures) the power consumption rate, after the external programming device obtains the power consumption rate, it then can display the power consumption rate using a graphical visual indicator (block 604). Upon displaying the power consumption rate, it can be determined if the power consumption is sub-optimal (block 606). In one embodiment, a physician might be able to determine that the power consumption rate is sub-optimal merely by looking at the graphical visual indicator. For example, as discussed above, a large number of bars or yellow or red colors might indicate that the IMD does not have optimal settings. In other embodiments, the external programming device can be configured to analyze the power consumption rate and determine if it is sub-optimal. In this embodiment, the external programming device can be configured to send a message or generate an alarm, informing the physician that the IMD setting might be sub-optimal. As one skilled in the art will appreciate, however, there may be times where it is necessary to set IMDs with high power consumption settings; for example with extreme heart conditions. Thus, in these situations, even if the power consumption is higher than normal or even high, it still might not be sub-optimal. Typically, it will be the physician that determines where the power consumption rate is sub-optimal based on many parameters, including power consumption rate, heart condition, required therapy, etc.

If it is determined that the power consumption rate is sub-optimal, a physician can adjust one or more IMD settings or parameters that might be contributing sub-optimal power consumption situation (block 608), for example by using the external programming device to adjust one or more IMD settings. As one skilled in the art will appreciate, such parameters can include, but are not limited to pulse width, pulse amplitude, lead impedance, and pacing rate. After adjustments are made, the IMD and/or the external programming device can then calculate the adjusted power consumption (block 610), which then can again be displayed using the graphical visual indicator (block 612). Parameter adjustments and recalculations can occur as many times as is necessary for the physician to determine that the setting are appropriate.

As one skilled in the art will appreciate, calculating the power consumption rate of an IMD is relatively straight forward, and in one embodiment, it merely relies on the parameters of the IMD itself. Also, there are a number of different methods and algorithms that can be used to calculate or determine an power consumption rate; some of which are device dependent. Thus, any device power consumption rate calculation algorithm or method can be used within the scope of the present invention. Further, in some embodiments, the external programming device and/or the IMD can measure or calculate the power consumption for the IMD using IMD parameters, such as lead impedance, pace or sense rate, programmed pulse width, programmed pulse amplitude, and/or load parameters of one or more sensors associated with the IMD. A few non-limiting examples of sensors that may affect the power consumption include an XL (excellerometer) sensor, a MV (minute ventilator) sensor, pressure sensors, temperature sensors, etc.

In one embodiment, the power consumption of an IMD may be directly measured by the PG and displayed by a graphical visual indicator. In another embodiment the power consumption may be calculated by the external programming device using several parameters for example lead impedance, percent pace and programmed pulse width and pulse amplitude. Once calculated, the power consumption rate may be displayed by a graphical visual indicator.

For example, in some embodiments, the power consumption rate for low or normal power consumption setting might be in the range of about 6 to about 30 μW (see FIGS. 7*a* and 8a). Further, the power consumption rate for a medium or slightly elevated power consumption settings might be in the range of about 25 to about 60 µW (see FIGS. 7b and 8b). Finally, in some embodiments, the power consumption rate displayed a high power consumption settings might be about 60 µW and above (see FIGS. 7c and 8c). These values may be displayed but may not be extremely useful to the typical healthcare provider, which is why the graphical visual indicator is important. The healthcare provider simply can look at the graphical visual indicator, and from the display, quickly decides if change or adjustment might be needed.

Referring now to FIG. 9, one example of a user interface display screen 900 is shown. In this particular embodiment, user interface display screen 900 includes both battery summary information 910 and battery detail information 920. As illustrated, battery summary information 910 includes a battery life gauge 912, a battery power consumption or throttle indicator 914, and perhaps additional information. As discussed above, battery power consumption or throttle indicator 914 can display power consumption rate using one or more different graph and/or color configurations. If the power consumption rate is too high, a physician can pull-up another screen to adjust parameters that might be contributing the sub-optimal power consumption rate. One embodiment of this is disclosed in U.S. patent application Ser. No. 10/915,903, filed on Aug. 10, 2004, and entitled "Systems and Methods for Managing the Longevity of an Implantable Medical Device Battery," the entirety of which is incorporated by reference herein for all purposes. In this manner, a physician and/or clinician can identify parameters affecting the power consumption, and can use the graphical visual indicator to determine how best to optimize or improve the power consumption rate. That is, a physician can modify the IMD by adjusting at least one contributing parameter of the sub-optimal power consumption rate and determine how changing the parameter affects the power consumption rate displayed on the graphical visual indicator. The physician can perform multiple combinations and permutations of parameter changes to test power consumption rate improvements, while still providing proper therapy to the patient. Once the physician determines a proper setting for the IMD, the external programming device can communicate the new settings to the IMD, which, in turn, will implement the changes.

One skilled in the art will appreciate that the methods and systems described herein can be applied to other implantable medical devices, including implantable defibrillators and cardiac resynchronization devices. Thus, the present invention is not limited to any particular IMD configuration. In addition, while the embodiment discussed above describes the external programming device as performing the steps necessary to calculate and display the power consumption rate, and even display sub-optimal power consumption rates, one skilled in the art will appreciate that in other embodiments, some or all of these functions could be performed within the IMD itself. In those embodiments, the external programming device would perform the functions that the IMD does not. In most cases, however, the external programming device will be used to display the power consumption rate to the user, and the external programming device will be used to adjust IMD parameters to optimize or improve the power consumption rate.

In conclusion, the present invention provides novel systems and methods for monitoring and displaying the power consumption rate of an IMD. While detailed descriptions of one or more embodiments of the invention have been given above, various alternatives, modifications, and equivalents will be apparent to those skilled in the art without varying from the spirit of the invention. Therefore, the above description should not be taken as limiting the scope of the invention, which is defined by the appended claims.

What is claimed is:

1. A method for managing power consumption of an implantable medical device ("IMD"), comprising:
    calculating a power consumption rate for the IMD; and
    displaying the power consumption rate using a graphical visual indicator.

2. The method as recited in claim 1, wherein the IMD is a cardiac rhythm management device selected from the group consisting of a pacemaker, an implantable cardioverter defibrillator ("ICD"), a pacer/defibrillator, and a cardiac resynchronization ("CRT") device.

3. The method as recited in claim 1, wherein the step of calculating a power consumption rate for the IMD comprises calculating a power consumption rate based on one or more parameters selected from the group consisting of lead impedance, pace percent, programmed pulse width, and programmed pulse amplitude.

4. The method as recited in claim 1, further comprising using the power consumption rate to determine whether the IMD battery longevity is sub-optimal.

5. The method as recited in claim 1, further comprising displaying one or more parameters that might be affecting the power consumption rate.

6. The method as recited in claim 1, further comprising:
    determining whether the power consumption rate is sub-optimal; and
    identifying one or more parameters that might be contributing to the sub-optimal power consumption rate.

7. The method as recited in claim 6, wherein an external programming device performs the identifying step.

8. The method as recited in claim 6, further comprising:
    adjusting at least one of one or more parameters that might be contributing to the sub-optimal power consumption rate;
    calculating an adjusted power consumption rate for the IMD using the at least one adjusted parameter; and
    displaying the adjusted power consumption rate on the graphical visual indicator.

9. The method as recited in claim 1, wherein the graphical visual indicator is selected from the group consisting of a level indicator, a multi-colored display, a gray-scale display, a multi-size indicator, a radial indicator and a pie indicator.

10. The method as recited in claim 9, wherein the graphical visual indicator comprises a three-color display.

11. The method as recited in claim 10, wherein the first color on the display indicates a power consumption rate, the second color on the display indicates an elevated power consumption rate, and the third color on the display indicates a high power consumption rate.

12. The method as recited in claim 1, wherein the graphical visual indicator comprises a multi-level display.

13. The method as recited in claim 12, wherein the first level on the display indicates a power consumption rate, the second level on the display indicates an elevated power consumption rate, and third level on the display indicates a high power consumption rate.

14. The method as recited in claim 12, wherein each level of the display comprises one or more level indicators within each level.

15. The method as recited in claim 12, wherein each level indicator is an indicator of a power consumption rate.

16. A method for managing power consumption of an implantable medical device ("IMD") comprising:

calculating a power consumption rate for the IMD using an IMD parameter that influences power consumption of the IMD, the IMD parameter having a first value;

displaying the power consumption rate and the IMD parameter on a graphical visual indicator;

adjusting the IMD parameter from the first value to a second value;

calculating an adjusted power consumption rate using the second value of the IMD parameter; and displaying the adjusted power consumption rate and the second value of the IMD parameter using the graphical visual indicator.

17. The method of claim 16, wherein the IMD parameter includes at least one of pulse width and pulse amplitude.

18. The method of claim 16, wherein the IMD parameter includes at least one of pace rate and sense rate.

19. The method of claim 16, wherein the IMD parameter includes at least one load parameter of one or more sensors associated with the IMD.

20. The method of claim 16, wherein the power consumption rate and the IMD parameter are displayed to a health care provider.

21. The method of claim 16, wherein a health care provider adjusts the IMD parameter from the first value to the second value upon an external programmer of the IMD analyzing the power consumption rate to determine that it is sub-optimal and the external programmer notifying the health care provider that the power consumption rate is suboptimal.

22. A method for managing power consumption of an implantable medical device ("IMD") comprising:

calculating a power consumption rate for the IMD using an IMD parameter that influences power consumption of the IMD, the IMD parameter having a first value, wherein the IMD parameter includes at least one load parameter of one or more sensors associated with the IMD;

displaying the power consumption rate and the IMD parameter on a graphical visual indicator;

adjusting the IMD parameter from the first value to a second value;

calculating an adjusted power consumption rate using the second value of the IMD parameter; and displaying the adjusted power consumption rate and the second value of the IMD parameter using the graphical visual indicator.

* * * * *